US 9,370,408 B2

(12) United States Patent
Wada et al.

(10) Patent No.: US 9,370,408 B2
(45) Date of Patent: Jun. 21, 2016

(54) VIBRATIONAL FREQUENCY ADJUSTMENT DEVICE AND WATER FLOW TYPE ORAL CAVITY CLEANING DEVICE USING SAME

(75) Inventors: Yukinori Wada, Takatsuki (JP); Masahiro Nishiura, Takatsuki (JP)

(73) Assignee: SUNSTAR SUISSE SA., Etoy (CH)

( * ) Notice: Subject to any disclaimer, the term of this patent is extended or adjusted under 35 U.S.C. 154(b) by 1156 days.

(21) Appl. No.: 13/390,599

(22) PCT Filed: Aug. 9, 2010

(86) PCT No.: PCT/JP2010/063476
§ 371 (c)(1),
(2), (4) Date: Mar. 5, 2012

(87) PCT Pub. No.: WO2011/021523
PCT Pub. Date: Feb. 24, 2011

(65) Prior Publication Data
US 2012/0156641 A1 Jun. 21, 2012

(30) Foreign Application Priority Data

Aug. 17, 2009 (JP) .................................. 2009-188411
Jun. 24, 2010 (JP) .................................. 2010-143299

(51) Int. Cl.
*A61C 17/02* (2006.01)
*F15B 15/06* (2006.01)
(Continued)

(52) U.S. Cl.
CPC ........... *A61C 17/0202* (2013.01); *A61C 17/028* (2013.01); *A61C 17/20* (2013.01); *A61C 17/22* (2013.01); *Y10T 74/18056* (2015.01); *Y10T 74/18288* (2015.01)

(58) Field of Classification Search
CPC .... A61C 17/02; A61C 17/0202; A61C 17/22; A61C 17/028; A61C 17/00; A61C 17/036; A61C 17/20; F16H 37/12; F16H 37/124; Y10T 74/18288; Y10T 74/18056; F04B 9/04; F04B 9/042; F04B 9/045; F15B 15/06; F15B 15/063; F15B 15/065; F15B 15/066

USPC .......... 92/136, 140; 74/25, 45, 47, 48, 49, 53, 74/54, 55; 417/313, 415, 569; 433/80–90, 433/119

See application file for complete search history.

(56) References Cited

U.S. PATENT DOCUMENTS

RE15,833 E * 5/1924 Tefft ....................... B60C 23/00
                                                        26/70
1,985,406 A * 12/1934 Galkin .................. F16D 41/066
                                                       192/12 B (Continued)

FOREIGN PATENT DOCUMENTS

JP          5-161663        6/1993
JP          8-33656         2/1996

(Continued)

OTHER PUBLICATIONS

International Search Report for International Application No. PCT/JP2010/063476 dated Oct. 12, 2010.

*Primary Examiner* — Rachel Young
*Assistant Examiner* — Christopher Miller
(74) *Attorney, Agent, or Firm* — Kratz, Quintos & Hanson, LLP (57) ABSTRACT

A vibrational frequency adjustment device comprises, as a vibrational frequency adjustment means (22): a first conversion means (40) which is provided with an input-side rotating member (41), an output-side rotating member (42), and a one-way clutch (44) for transmitting only the rotational motion in one direction of the input-side rotating member (41) to the output-side rotating member (42) and which, by causing the input-side rotating member (41) to pivot in a reciprocating manner by a set angle by means of the reciprocating linear motion of an output shaft (10), transmits only the forward motion or the reverse motion of the input-side rotating member (41) to the output-side rotating member (42) through the one-way clutch (44) to thereby rotate the output-side rotating member (42) by a given angle; and a second conversion means (50) which converts the rotational motion of the output-side rotating member (42) into the reciprocating linear motion of a second shaft member (43).

21 Claims, 10 Drawing Sheets

(51) Int. Cl.
    *A61C 17/028*    (2006.01)
    *A61C 17/20*      (2006.01)
    *A61C 17/22*      (2006.01)

(56) References Cited

U.S. PATENT DOCUMENTS

| | | | | |
|---|---|---|---|---|
| 3,029,327 | A * | 4/1962 | Karl | H01H 3/22 310/23 |
| 4,146,020 | A * | 3/1979 | Moret | A61C 17/0202 15/22.1 |
| 4,979,503 | A | 12/1990 | Chernack | |
| 5,311,633 | A | 5/1994 | Herzog | |
| 5,634,791 | A * | 6/1997 | Matsuura | A61C 17/02 433/87 |
| 2002/0056365 | A1 * | 5/2002 | Jones | F01B 9/042 92/13 |
| 2004/0209222 | A1 * | 10/2004 | Snyder | A61C 17/02 433/80 |
| 2008/0008979 | A1 * | 1/2008 | Thomas | A61C 17/0202 433/80 |
| 2013/0061744 | A1 * | 3/2013 | Celotta | F04B 9/042 92/140 |

FOREIGN PATENT DOCUMENTS

| | | |
|---|---|---|
| JP | 11-128252 | 5/1999 |
| JP | 2002-176758 A1 | 6/2002 |
| JP | 2002-534209 A1 | 10/2002 |
| JP | 2007-215796 A1 | 8/2007 |
| JP | 2008-29659 A1 | 2/2008 |
| WO | WO 2004/112536 A1 | 12/2004 |

\* cited by examiner

VIBRATIONAL FREQUENCY ADJUSTMENT DEVICE AND WATER FLOW TYPE ORAL CAVITY CLEANING DEVICE USING SAME

TECHNICAL FIELD

The present invention relates to a vibrational frequency adjustment device for adjusting the vibrational frequency of reciprocating linear motion and a water flow type oral cavity cleaning device using the same.

BACKGROUND ART

As an electric toothbrush with a cleaning head making a reciprocating linear motion, a motor-powered electric toothbrush including conversion means that converts rotation of a pinion fixedly attached to a rotation shaft of a motor into rotation of a face gear about an axial core orthogonal to the rotation shaft and then converts the rotation of the face gear into reciprocating linear motion of a drive shaft via a crank shaft, is widely employed because of its low-cost manufacturability. However, in the motor-powered electric toothbrush, the face gear is rotated at a reduced speed by engagement of gear wheels, and thus the cleaning head is set with a vibrational frequency of 1,500 to 5,000 cpm and an amplitude of 3 to 7 mm, whereby there is a limit for providing the cleaning head with a high vibrational frequency. Accordingly, so-called sonic electric toothbrushes having a cleaning head with a vibrational frequency of 5,000 to 11,000 cpm and an amplitude of 0.2 to 1.0 mm, have recently been suggested and put into practical use, in which a plurality of gears is combined (refer to Patent Document 1, for example), a scotch yoke mechanism is used (refer to Patent Document 2, for example), or a linear actuator having a permanent magnet and a coil is used (refer to Patent Document 3, for example).

Meanwhile, as an oral cavity cleaning device, there is put into commercial use a water flow type oral cavity cleaning device including a pump capable of discharging a cleaning liquid by reciprocating linear motion of a piston; pump drive means driving the piston; and a discharge nozzle for the cleaning liquid, in which the cleaning liquid can be intermittently injected from the nozzle to thereby efficiently clean interdental gaps and periodontal pockets with the cleaning liquid (refer to Patent Document 4, for example).

In addition, as a water flow type oral cavity cleaning device, there is suggested a water flow type oral cavity cleaning device in which a connection member capable of being connected to a drive shaft of a drive unit of a motor-powered electric toothbrush is provided so that a pump can be driven by the drive unit of the motor-powered electric toothbrush, whereby pump drive means of the water flow type oral cavity cleaning device can be used also as a drive unit of a motor-powered electric toothbrush (refer to Patent Document 5, for example).

CITATION LIST

Patent Literature

Patent Document 1: WO 2004/112536
Patent Document 2: JP-A No. 2007-215796
Patent Document 3: JP-A No. 2002-176758
Patent Document 4: JP-A No. 11-128252
Patent Document 5: JP-A No. 5-161663

SUMMARY OF INVENTION

Technical Problem

The invention disclosed in Patent Document 5 allows a drive unit of a motor-powered electric toothbrush to be used also as the pump drive means of the water flow type oral cavity cleaning device, and therefore the water flow type oral cavity cleaning device can be utilized with reduction in economic burden on a user by using a drive unit of a currently used electric toothbrush as the pump drive means of the water flow type oral cavity cleaning device. However, when a drive unit of a sonic electric toothbrush, instead of a motor-powered electric toothbrush, is connected to the water flow type oral cavity cleaning device, it is not possible to provide a sufficient discharge amount of the cleaning liquid due to a short stroke of the drive shaft of 0.2 to 1.0 mm, for example, and it is not possible to allow a piston of the pump to make a reciprocating linear motion at a high vibrational frequency of 5,000 to 11,000 cpm, which makes the water flow type oral cavity cleaning device unpractical. In addition, it is obvious that sonic electric toothbrushes use piston-type pumps due to a short stroke of the drive shaft, and even using diaphragm pumps cannot provide a sufficient discharge amount of cleaning liquid. Accordingly, it is considered as being extremely difficult to use a drive unit of a sonic electric toothbrush also as a pump drive means of water flow type oral cavity cleaning device.

Accordingly, an object of the present invention is to provide a vibrational frequency adjustment device that realizes easy adjustment of the vibrational frequency and amplitude of a reciprocating linear motion by a simple mechanical configuration, and a water flow type oral cavity cleaning device that uses the vibrational frequency adjustment device to thereby allow pump drive means to be used also as a drive unit of a sonic electric toothbrush.

Solution to Problem

A vibrational frequency adjustment device of the present invention includes first conversion means that includes an input-side rotational member, an output-side rotational member, and a one-way clutch transferring only a rotational motion of the input-side rotational member in one direction to the output-side rotational member, and allows the input-side rotational member to make a reciprocating rotational motion by a set angle by a reciprocating linear motion of a first shaft member, thereby to transfer only a forward motion or a backward motion of the input-side rotational member to the output-side rotational member via the one-way clutch and rotate the output-side rotational member by each specific angle; and second conversion means that converts the rotational motion of the output-side rotational member into a reciprocating linear motion of a second shaft member.

In the vibrational frequency adjustment device, when the first shaft member makes a reciprocating linear motion, the input-side rotational member of the first conversion means makes a reciprocating rotational motion by a set angle, only a forward motion or a backward motion of the input-side rotational member is transferred to the output-side rotational member via the one-way clutch, and then the output-side rotational member rotates by each specific angle. In addition, the second conversion means converts the rotation of the output-side rotational member into a reciprocating linear motion of the second shaft member, whereby the second shaft member makes one reciprocating linear motion each time the first shaft member makes a plurality of reciprocating linear motions and the output-side rotational member makes one rotation. For example, if the output-side rotational member rotates by 30 degrees by one reciprocating motion of the first shaft member, the second shaft member makes one reciprocating linear motion by 12 reciprocating linear motions of the first shaft member, which allows the vibrational frequency of the second shaft member to be adjusted to $\frac{1}{12}$ of the vibrational frequency of the first shaft member. In this manner, in the vibrational frequency adjustment device, the vibrational frequency of the second shaft member can be adjusted inexpensively and reliably by employing a simple mechanical configuration having the one-way clutch as the first conversion means. In addition, the second conversion means uses a crank mechanism or a cam mechanism or the like to convert a rotational motion of the output-side rotational member into a reciprocating motion of the second shaft member, and the second conversion means also makes it possible to arbitrarily adjust the amplitude of the second shaft member.

In a preferred embodiment, the first conversion means is provided with a lever member that converts a reciprocating linear motion of the first shaft member into a reciprocating rotational motion of the input-side rotational member. In this case, adjusting a lever length of the lever member makes it possible to adjust the angle of a reciprocating rotational motion of the input-side rotational member at a reciprocating linear motion of the first shaft member and adjust the ratio of the vibrational frequency of the first shaft member and the vibrational frequency of the second shaft member.

The second conversion means may be configured in such a manner that a first gear is formed at an outer peripheral part of the output-side rotational member; a second gear engaging with the first gear is provided; and an eccentric cam allowing the second shaft member to make a reciprocating linear motion is arranged at the second gear. In this case, the number of reciprocating linear motions of the second shaft member at one rotation of the output-side rotational member can be altered by changing the ratio of number of teeth between the first gear and the second gear. In addition, the amplitude of the second shaft member can be regulated by adjusting an eccentric distance of the eccentric cam.

A water flow type oral cavity cleaning device of the present invention includes: a pump capable of discharging a cleaning liquid by a reciprocating linear motion of a piston; pump drive means driving the piston; and a discharge nozzle for the cleaning liquid, in which the pump drive means includes the vibrational frequency adjustment device and a drive means main body having a first shaft member making a reciprocating linear motion, the input-side rotational member is allowed to make a reciprocating rotational motion by a set angle by a reciprocating linear motion of the first shaft member, thereby to transfer only a forward motion or a backward motion of the input-side rotational member to the output-side rotational member via the one-way clutch and rotate the output-side rotational member by each specific angle, and the rotational motion of the output-side rotational member is converted into a reciprocating linear motion of the second shaft member, thereby to allow the piston to make a reciprocating linear motion at the second shaft member.

In the water flow type oral cavity cleaning device, a reciprocating linear motion of the first shaft member in the drive means main body is switched to a reciprocating linear motion of the second shaft member in the vibrational frequency adjustment device, whereby the piston of the pump can be driven by the second shaft member. In the vibrational frequency adjustment device, the vibrational frequency and amplitude of a reciprocating linear motion of the second shaft member can be arbitrarily adjusted as described above. Accordingly, it is possible to adjust a reciprocating linear motion of the first shaft member vibrating at a high speed to a low-speed reciprocating linear motion of the second shaft member, for example, and use a drive unit of a sonic electric toothbrush also as the drive means main body of the water flow type oral cavity cleaning device.

In a preferred embodiment, the drive means main body is used also as a drive unit of a sonic electric toothbrush. In this configuration, the water flow type oral cavity cleaning device can be driven by the drive unit of the currently used sonic electric toothbrush, thereby to reduce an economic burden on a user of the sonic electric toothbrush at introduction of the water flow type oral cavity cleaning device.

The first shaft member and the nozzle can be arranged in a coaxial line. In general, the first shaft member is arranged coaxially with a replacement brush of a sonic electric toothbrush. The nozzle of the water flow type oral cavity cleaning device, is supposed to be inserted into an oral cavity of a user for use as with the replacement brush. Therefore, the nozzle can be enhanced in operability at use of the water flow type oral cavity cleaning device by arranging the first shaft member and the nozzle in a coaxial line to meet the same positional relationship as that of the first shaft member and the replacement brush.

A pump and a cleaning liquid tank can be provided above a handling grip part. Although the cleaning liquid tank may be provided at the grip part or under the same, the cleaning liquid has a larger pressure loss in the course from the cleaning liquid tank to the pump and in the course from the pump to the nozzle. Therefore, the pump and the cleaning liquid tank are preferably provided above the handling grip part.

In another preferred embodiment, a drive unit of an electric toothbrush including a drive shaft as the first shaft member making a reciprocating linear motion, is detachably provided as the drive means main body to a cleaning device main body having the pump, the discharge nozzle, and the vibrational frequency adjustment device, and a power transfer attachment transferring power of the drive unit to the first conversion means, is provided, the power transfer attachment including: a power transfer member that has a fitting part fitted and fixed detachably to the first shaft member of the drive unit and transfers power of the first shaft member to the first conversion means; and position adjustment means that moves the drive unit and the cleaning device main body relatively in an axial direction of the first shaft member, thereby to adjust the current position of a reciprocating linear motion of the power transfer member moving together with the first shaft member of the drive unit with respect to the cleaning device main body to a position adapted to the current position of a reciprocating motion of the first shaft member with respect to the drive unit.

In this case, the first shaft member formed by the drive shaft of the drive unit of the electric toothbrush is fitted and fixed to the fitting part of the power transfer member of the attachment, and power of the first shaft member is transferred via the power transfer member to the cleaning device main body. When the first shaft member is inserted and fitted into the fitting part of the power transfer member, even if the power transfer member is pressed and moved toward a top dead point, the position adjustment means allows the drive unit and the cleaning device main body to move relatively in the axial direction of the first shaft member, and the current position of a reciprocating linear motion of the power transfer member moving together with the first shaft member with respect to the cleaning device main body is adjusted to a position adapted to the current position of a reciprocating linear motion of the first shaft member with respect to the drive unit. Accordingly, the reciprocating linear motion of the first shaft member with respect to the drive unit and the reciprocating linear motion of the power transfer member with respect to the cleaning device main body, are synchronized.

As in the foregoing, the power transfer attachment allows the position adjustment means to synchronize by a one-touch operation a reciprocating linear motion of the first shaft member with respect to the drive unit and a reciprocating linear motion of the power transfer member with respect to the cleaning device main body. This makes it possible to eliminate an adjustment for synchronization and allow the water flow type oral cavity cleaning device to be used only by fitting the first shaft member into the fitting part of the power transfer member.

If using the thus configured power transfer attachment, in a preferred embodiment, the first conversion means is provided with a lever member converting a reciprocating linear motion of the first shaft member into a reciprocating rotational motion of the input-side rotational member, and the power transfer member is coupled to an end part of the lever member. In this case, adjusting a lever length of the lever member makes it possible to adjust the angle of a reciprocating rotational motion of the input-side rotational member at a reciprocating linear motion of the first shaft member and regulate the ratio between vibrational frequency of the first shaft member and vibrational frequency of the second shaft member.

In addition, the position adjustment means may include first bias means that is compressed by a fitting operation of the first shaft member into the fitting part to bias the drive unit in a direction of separation of the first shaft member; and a positioning means that locks movement of the drive unit by the first bias means in the direction of separation and places the drive unit in an appropriate position with respect to the cleaning device main body. In this case, the first shaft member can be reliably fitted and fixed to the fitting part by fitting the first shaft member to the fitting part of the power transfer member while compressing the first bias means. In addition, after the fitting of the first shaft member, the drive unit is moved together with the first shaft member and the power transfer member in the direction separation of the first shaft member by a bias force of the first bias means, the drive unit is placed by the positioning means in a position appropriate with respect to the cleaning device main body, and the current position of a reciprocating linear motion of the power transfer member with respect to the cleaning device main body is adjusted to a position adapted to the current position of a reciprocating linear motion of the first shaft member with respect to the drive unit. Accordingly, the reciprocating linear motion of the first shaft member with respect to the drive unit and the reciprocating linear motion of the power transfer member with respect to the cleaning device main body, are synchronized.

In another preferred embodiment, second bias means is provided to bias the power transfer member making a reciprocating linear motion together with the first shaft member to a central position of a reciprocating linear motion of the power transfer member. Providing the second bias means is preferred in stabilizing an operation of the power transfer member.

A guide part guiding the drive unit movably only in a direction of fitting of the first shaft member to the fitting part, may be provided. In this case, moving the drive unit along the guide part makes it possible to facilitate insertion and extraction of the first shaft member from and into the fitting part.

Advantageous Effects of Invention

In the vibrational frequency adjustment device of the present invention, the vibrational frequency of the second shaft member can be adjusted inexpensively and reliably by employing the first conversion means of a simple mechanical configuration having a one-way clutch. In addition, the second conversion means uses a crank mechanism, a cam mechanism, or the like, to convert a rotational motion of the output-side rotational member into a reciprocating motion of the second shaft member. The second conversion means also allows the amplitude of the second shaft member to be arbitrarily adjusted.

In the water flow type oral cavity cleaning device of the present invention, the vibrational frequency adjustment device makes it possible to arbitrarily adjust the vibrational frequency and amplitude of a reciprocating linear motion of the second shaft member. This makes it possible to adjust a reciprocating linear motion of the first shaft member vibrating at a high speed to a low-speed reciprocating linear motion of the second shaft member, and use a drive unit of a sonic electric toothbrush also as the drive means main body of the water flow type oral cavity cleaning device.

DESCRIPTION OF EMBODIMENTS

An embodiment for carrying out the present invention will be described below with reference to the drawings.

As shown in FIGS. 1 to 4, a water flow type oral cavity cleaning device 1 includes a cleaning device main body 2, and a drive unit 3 as a drive means main body detachably attached to a front side of the cleaning device main body 2, in which a drive unit of a sonic electric toothbrush is used also as the drive unit 3 of the water flow type oral cavity cleaning device 1. In the following description of this embodiment, a side of the device on which the drive unit 3 is attached is defined as a front side.

The drive unit 3 includes a drive shaft 10 (equivalent to a first shaft member) supported so as to be capable of a reciprocating linear motion; a motor 12 driven by a battery 11; and a scotch yoke mechanism 13 that converts a rotational motion of a rotation shaft 12a of the motor 12 into a reciprocating linear motion of the drive shaft 10. The drive unit 3 is configured in the same manner as a drive unit of a well-known sonic electric toothbrush, where a replacement brush (not shown) can be detachably attached to an upper end portion of the drive shaft 10, and the drive shaft 10 makes one reciprocating motion each time the rotation shaft 12a makes one rotation by the scotch yoke mechanism 13. However, the drive unit 3 may be used as a drive unit of an arbitrarily configured sonic electric toothbrush with an increased vibrational frequency of the drive shaft 10 by combining a plurality of gears or by the use of a linear actuator having a permanent magnet and a coil, or may be used as a drive unit of a motor-powered electric toothbrush with a low vibrational frequency of the drive shaft 10 of 1,500 to 5,000 cpm, as far as the drive unit 3 is configured to allow the drive shaft 10 to make a reciprocating linear motion.

As shown in FIGS. 1 to 7, the cleaning device main body 2 includes: a power transfer attachment 60 that transfers power of the drive shaft 10 of the drive unit 3 to the cleaning device main body 2 via a power transfer member 61; a pump 21 that is capable of discharging a cleaning liquid by a reciprocating linear motion of a piston 20; vibrational frequency adjustment means 22 that switches a reciprocating linear motion of the power transfer member 61 to a reciprocating linear motion of the piston 20 with a vibrational frequency and an amplitude adapted to the pump 21; a cleaning liquid tank 23 storing the cleaning liquid; and a discharge nozzle 24 for the cleaning liquid. The cleaning device main body 2 is configured to clean interdental gaps, tooth surfaces, periodontal pockets, and the like, by the cleaning liquid discharged intermittently from the discharge nozzle 24. The vibrational frequency adjustment means 22 is equivalent to the vibrational frequency adjustment device, and the vibrational frequency adjustment means 22 and the drive unit 3 are equivalent to the pump drive means.

Formed on an upper part of a frame 25 of the cleaning device main body 2 is a U-shaped and horseshoe-like base part 26 in a planar view over which the cleaning liquid tank 23 is detachably fitted. Formed under the frame 25 is a grip part 27 extending to a lower end of the drive unit 3 along a back side of the same. The grip part 27 is configured to improve operability of the cleaning device 1 by gripping by hand the drive unit 3 together with the grip part 27.

The discharge nozzle 24 is formed by a well-known, hollow and pipe-like discharge nozzle for water pickup, and is detachably attached to an upper end of the base part 26 in a liquid-tight manner so as to be coaxial with the drive shaft 10.

The pump 21 includes a circular cylinder 30 provided in an up-down direction within a lower portion of the base part 26; the piston 20 fitted into the cylinder 30 in a liquid-tight manner so as to be capable of up-down movement; and a valve member 32 capable of opening and closing an entrance part 31 at a lower end portion of the cylinder 30. The pump 21 is connected to a supply tube 33 allowing a lower end of the cleaning liquid tank 23 and the entrance part 31 of the cylinder 30 to communicate with each other, and is connected to a discharge tube 35 allowing an exit part 34 at a lower part of the cylinder 30 and the discharge nozzle 24 to communicate with each other. When the piston 20 moves upward, the valve member 32 is opened and the cleaning liquid in the cleaning liquid tank 23 is supplied to the cylinder 30 through the supply tube 33. When the piston 20 moves downward, the valve member 32 is closed and the cleaning liquid in the cylinder 30 is discharged from the discharge nozzle 24 through the discharge tube 35.

The vibrational frequency adjustment means 22 includes first conversion means 40 that converts a reciprocating linear motion of the power transfer member 61 making a reciprocating linear motion together with the drive shaft 10 into a rotational motion of an output-side rotational member 42 in one direction; and second conversion means 50 that converts the rotational motion of the output-side rotational member 42 into a reciprocating linear motion of a second shaft member 43.

Figure 5:
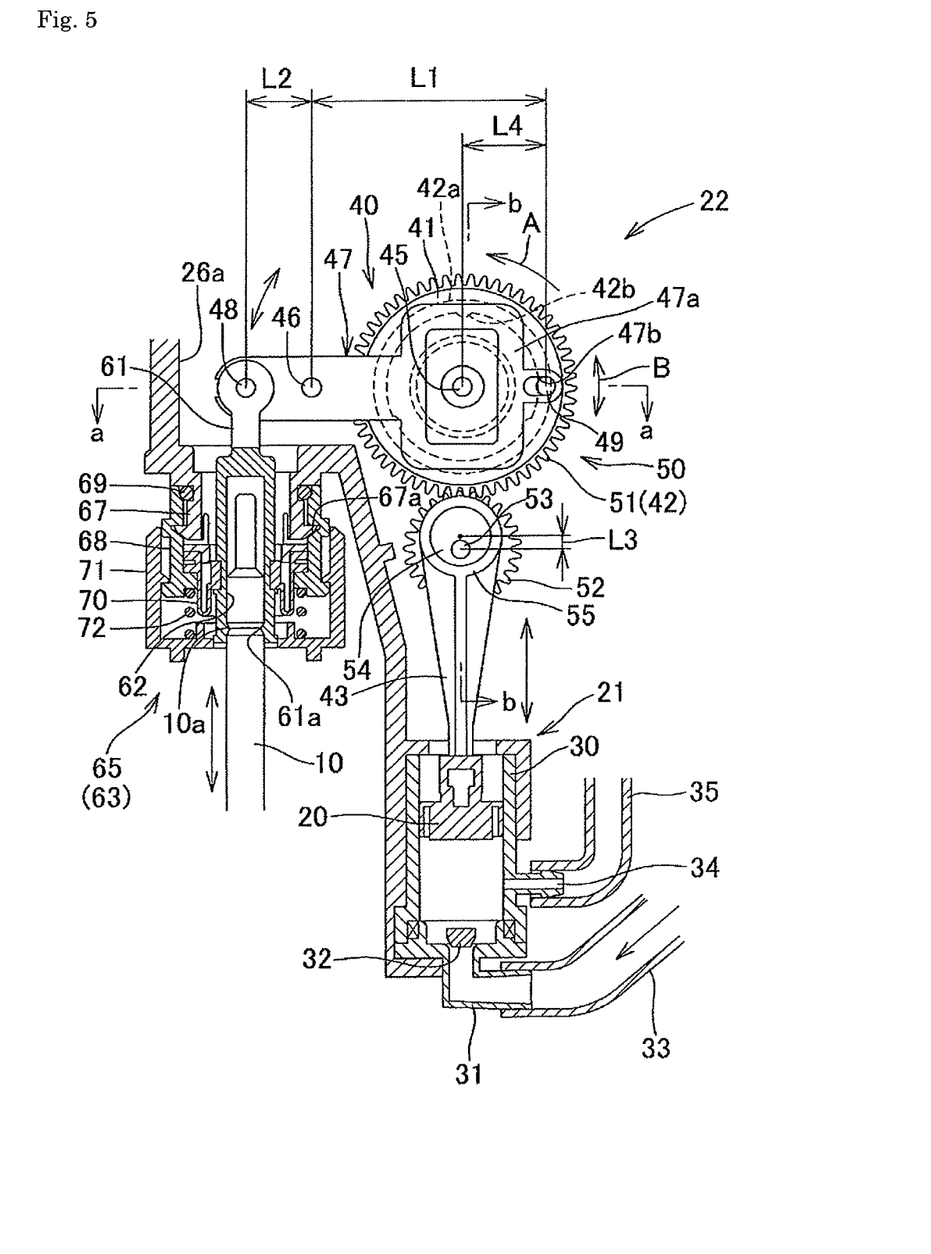
FIG. 5 is a diagram for describing an operation of a vibrational frequency adjustment device and a pump in the water flow type oral cavity cleaning device.
Figure 6:
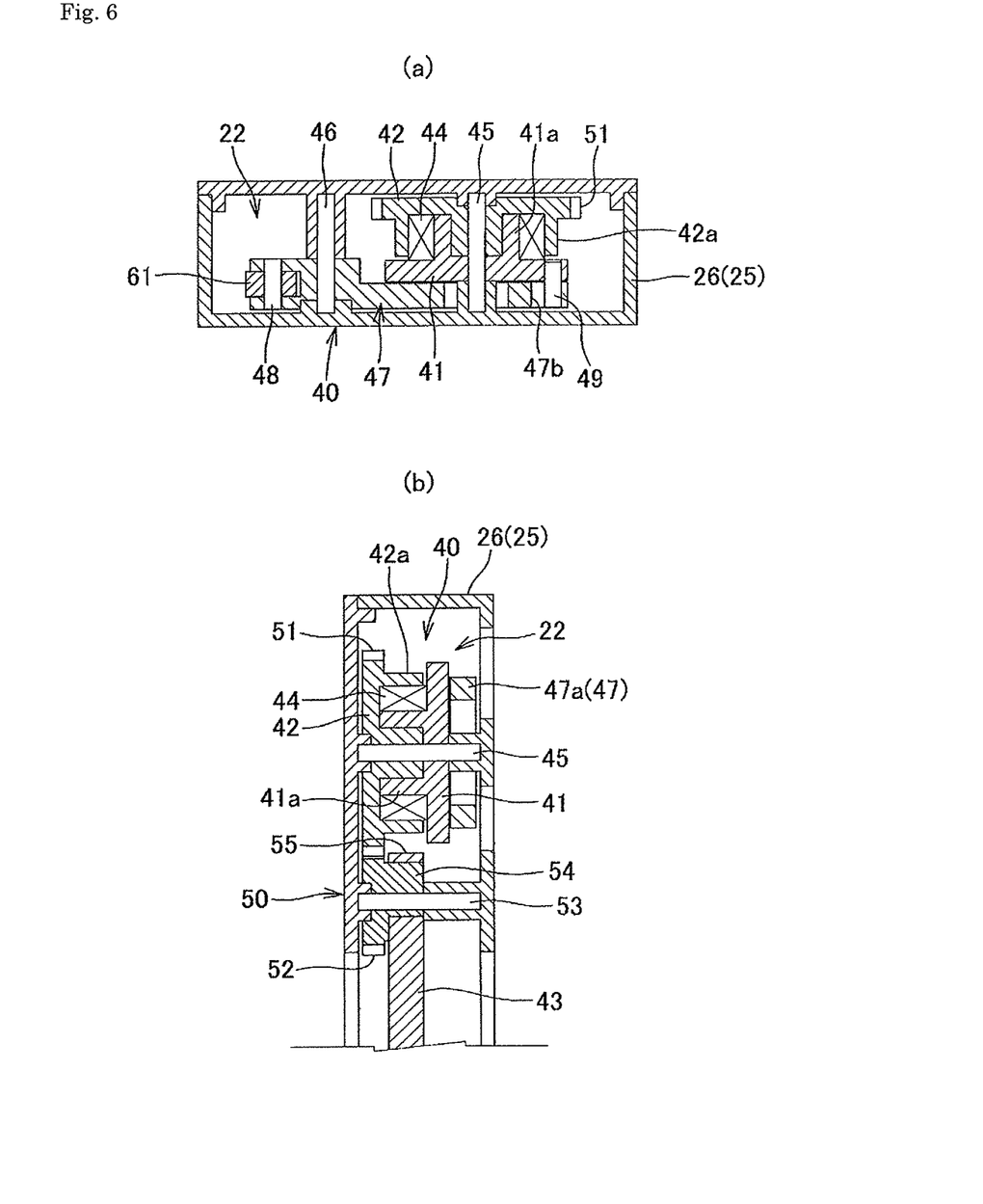
FIG. 6(a) is a cross section view of FIG. 5 taken along line a-a.
FIG. 6(b) is a cross section view of FIG. 5 taken along line b-b.
Figure 7:
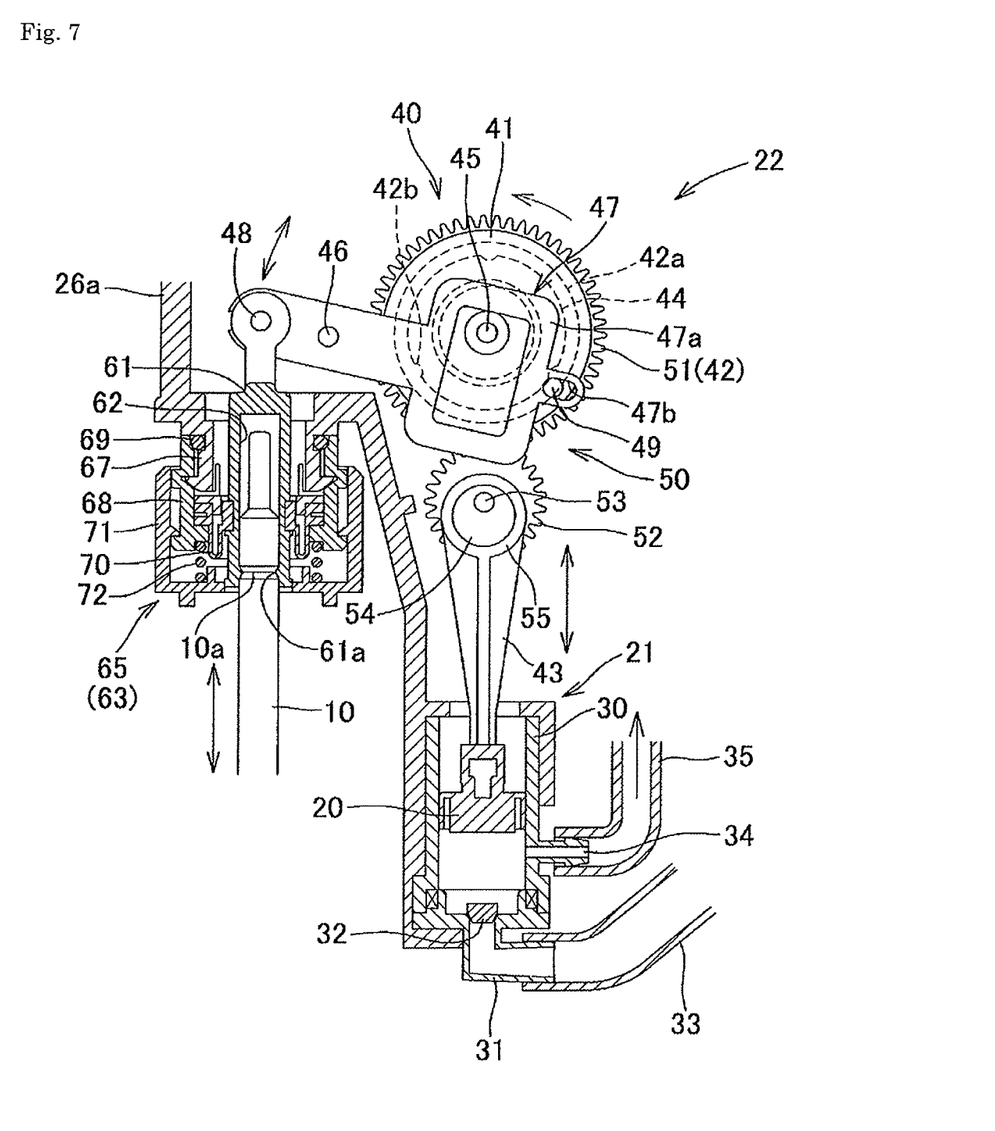
FIG. 7 is a diagram for describing an operation of a vibrational frequency adjustment device and a pump in the water flow type oral cavity cleaning device.

As shown in FIGS. 5 to 7, the first conversion means 40 includes an input-side rotational member 41; the output-side rotational member 42; and a one-way clutch 44 that transfers a rotational motion of the input-side rotational member 41 only in one direction to the output-side rotational member 42. The input-side rotational member 41, the output-side rotational member 42, and the one-way clutch 44 are rotatably supported via a support shaft 45 in an upper back portion of the base part 26.

The first conversion means 40 will be described below. The first conversion means 40 is provided with the ring-like one-way clutch 44 of a well-known configuration in which a plurality of axially extending rollers (not shown) is circumferentially arranged on an inner peripheral part so as to appear at specific intervals; an input-side sleeve 41a over which the one-way clutch 44 is fitted is formed to project at a central part of the disc-like input-side rotational member 41; and an output-side sleeve 42a fitted over the one-way clutch 44 and formed to project in the proximity of an outer periphery of the disc-like output-side rotational member 42. The input-side rotational member 41 is fitted into the one-way clutch 44 so as to be incapable of relative rotation in a direction shown by arrow A and be capable of relative rotation in a direction opposite to the direction shown by arrow A. The output-side rotational member 42 is fitted over the one-way clutch 44 so as to be incapable of relative rotation via a projection 42b projecting on an inner peripheral surface of the output-side rotational member 42. In addition, at rotation of the input-side rotational member 41 in the direction of arrow A, the output-side rotational member 42 rotates together with the input-side rotational member 41 via the one-way clutch 44, and a rotating force of the input-side rotational member 41 is transferred to the output-side rotational member 42. At rotation of the input-side rotational member 41 in the direction opposite to arrow A, only the input-side rotational member 41 rotates, and no rotating force is transferred to the output-side rotational member 42 via the one-way clutch 44.

A lever member 47 extending in a front-back direction is provided at an upper portion of the base part 26, so as to be rotatable about a horizontal pivotal support shaft 46. A front end portion of the lever member 47 is rotatably coupled to the power transfer member 61 capable of being integrally fitted over the drive shaft 10 via a pin member 48, a middle portion of the lever member 47 has a frame portion 47a avoiding contact with a support shaft 45 of the first conversion means 40, and a back end portion of the lever member 47 has a horizontally elongated long hole 47b. An operation pin 49 is raised and fixed so as to be fitted into the long hole 47b in the proximity of an outer periphery of the input-side rotational member 41. When the lever member 47 rotates about the pivotal support shaft 46 by a reciprocating linear motion of the drive shaft 10 in an up-down direction, the amplitude of the drive shaft 10 is amplified depending on the ratio of a length L1 between the pivotal support shaft 46 and the operation pin 49 and a length L2 between the pivotal support shaft 46 and the pin member 48, and the back end portion of the lever member 47 makes a reciprocating motion in the up-down direction. Then, when the input-side rotational member 41 makes a reciprocating rotational motion by an angle corresponding to the amplitude of the back end portion of the lever member 47 as shown by arrow B, the output-side rotational member 42 rotates via the one-way clutch 44 by each specific angle in the direction of arrow A. However, the long hole 47b may be formed in the input-side rotational member 41, and the operation pin 49 may be provided at the lever member 47.

The second conversion means 50 will be described below. A first gear 51 is formed at an outer peripheral portion of the output-side rotational member 42, and a second gear 52 engaging with the first gear 51 is supported at a lower side of the output-side rotational member 42 so as to rotatable about the pin member 53, and a cylindrical eccentric cam 54 is provided at the second gear 52 so as to be eccentric by a specific distance L3 with respect to the pin member 53. A tubular part 55 rotatably fitted over the eccentric cam 54 is formed at an upper end portion of the second shaft member 43 driving the piston 20 of the pump 21 in the up-down direction. When the second gear 52 rotates about the pin member 53, the second shaft member 43 and the piston 20 make a reciprocating linear motion in the up-down direction with an amplitude twice the eccentric distance L3 of the eccentric cam 54 with respect to the pin member 53.

At the oral cavity cleaning device 1, it is possible to set the ratio between vibrational frequency of the first shaft member and the vibrational frequency of the second shaft member 43 depending on the ratio between lengths L1 and L2 of the lever member 47 of the first conversion means 40, a distance L4 between the operation pin 49 and the support shaft 45, and the ratio of number of teeth between the first gear 51 and the second gear 52. In addition, the amplitude of a reciprocating linear motion of the piston 20 is twice larger than the eccentric distance L3 of the eccentric cam 54. Therefore, it is possible to use a drive unit of a sonic electric toothbrush also as the drive unit 3 of the water flow type oral cavity cleaning device 1, even if the drive shaft 10 has a vibration frequency of is 5,000 to 11,000 cpm and an amplitude of 0.2 to 1.0 mm. However, the pump 21, the vibrational frequency adjustment means 22, the cleaning liquid tank 23, and the discharge nozzle 24 may be configured in manners other than those shown in FIGS. 1 to 7.

As shown in FIGS. 1 to 5 and 7 to 10, the power transfer attachment 60 has a fitting part 62 detachably fitted and fixed to the drive shaft 10 of the drive unit 3, and includes a power transfer member 61 transferring power of the drive shaft 10 to the cleaning device main body 2; and position adjustment means 63 that moves the drive unit 3 and the cleaning device main body 2 relatively in an axial direction (up-down direction) of the drive shaft 10 and adjusts the current position of a reciprocating linear motion of the power transfer member 61 moving together with the drive shaft 10 of the drive unit 3 to a position adapted to the current position of a reciprocating linear motion of the drive shaft 10 with respect to the drive unit 3.

The position adjustment means 63 includes: a pair of right and left guide parts 64 guiding the drive unit 3 movably only in the up-down direction; first bias means 65 that is compressed by a fitting operation of the drive shaft 10 to the fitting part 62 to bias the drive unit 3 in a direction of separation of the drive shaft 10 (downward in FIG. 5); and positioning means 66 that locks movement of the drive unit 3 by the first bias means 65 in the direction of separation and places the drive unit 3 in an appropriate position with respect to the cleaning device main body 2.

The guide parts 64 are formed to project forward in an arc-like shape from the right and left sides of the grip part 27 along the drive unit 3 arranged in front of the grip part 27 of the cleaning device main body 2. The drive unit 3 is guided movably only in the up-down direction when being inserted between the right and left guide parts 64 from underneath. However, the guide parts 64 may be omitted.

The first bias means 65 will be described below. As shown in FIGS. 5, and 7 to 10, a downwardly projecting support tubular part 67 is integrally formed on a lower surface of the front portion 26a of the base part 26 opposed to the drive unit 3. The support tubular part 67 has hook parts 67a circumferentially spaced at a heightwise middle portion, and a downwardly extending coupling tube 68 is fitted over and fixed to fitting concave parts 68a so as to be engaged with the hook parts 67a and be incapable of moving in the up-down direction. An O-ring 69 is intervened between a base end portion of the support tubular part 67 and an upper end portion of the coupling tube 68, and the coupling tube 68 is fitted over the support tubular part 67 via the O-ring 69 in watertight manner.

The power transfer member 61 is provided so as to pass through vertically central portions of the support tubular part 67 and the coupling tube 68. The coupling tube 68 has inwardly projecting annular holding parts 68b at a lower end portion thereof, second bias means 70 formed by a disc-like rubber member is provided between the holding part 68b and a lower end portion of the support tubular part 67. A middle portion of the power transfer member 61 penetrates through and is fixed to central portion of the second bias means 70. The second bias means 70 biases the power transfer member 61 constantly to a central position of a reciprocating linear motion, and closes gaps between the support tubular part 67 and the power transfer member 61 and between the coupling tube 68 and the power transfer member 61, in a water-tight manner.

An annular groove 68c is formed in an outer peripheral surface of the coupling tube 68 at a heightwise middle portion, and three vertically extending guide grooves 68d are spaced circumferentially in the outer peripheral surface of the coupling tube 68. A cylindrical pressure tube 71 is fitted over the coupling tube 68 movably in the vertical direction. Engagement projections 71a are formed in an inner peripheral surface of the pressure tube 71 so as to engage with the annular groove 68c movably in the vertical direction. Projecting rails 71b are circumferentially spaced in the internal peripheral surface of the pressure tube 71 so as to be fitted into the guide grooves 68d. The pressure tube 71 is externally attached to the coupling tube 68 so as to be incapable of relative movement in a circumferential direction and be capable of vertical movement by a groove width of the annular groove 68c. An inwardly extending annular reception part 71c is formed at a lower end portion of the pressure tube 71. A spring member 72 biasing the pressure tube 71 constantly downward is provided between the holding part 68b of the coupling tube 68 and the reception part 71c of the pressure tube 71. Alternatively, in place of the spring member 72, synthetic rubber such as urethane rubber or a cushion material such as an air cushion, can be provided.

Figure 1:
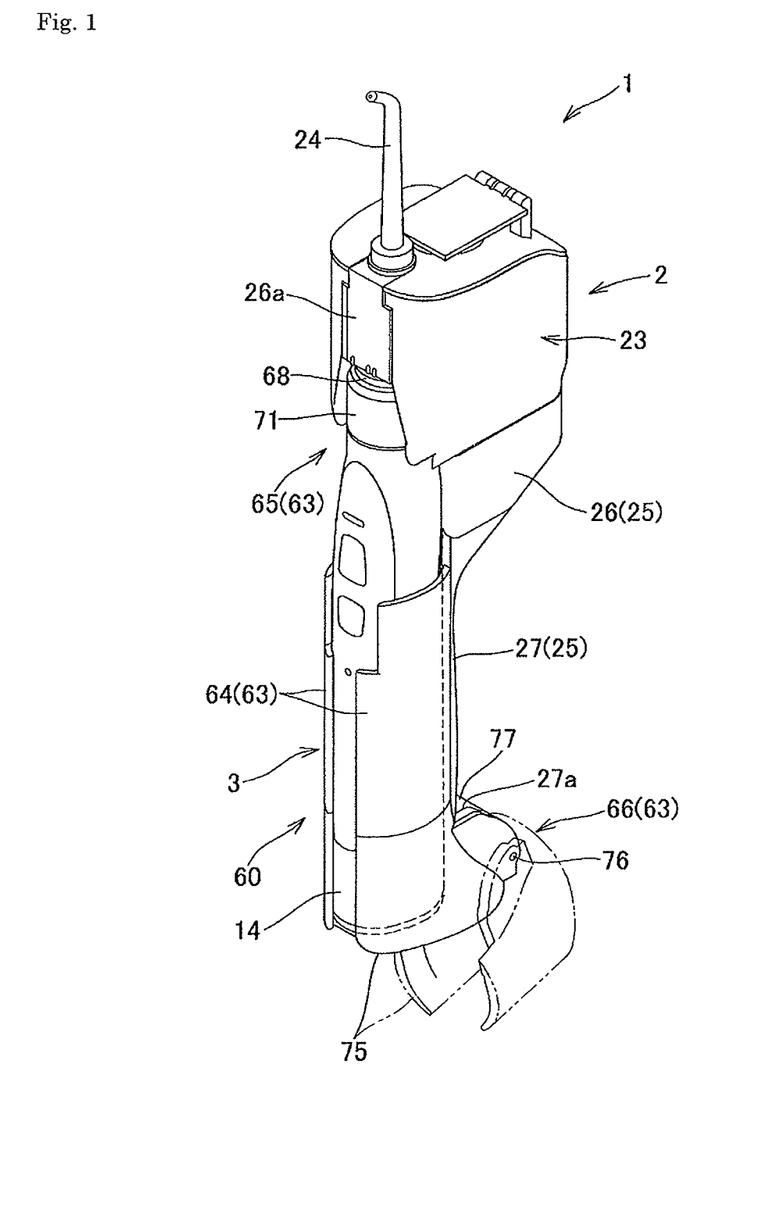
FIG. 1 is a perspective view of a water flow type oral cavity cleaning device.
Figure 2:
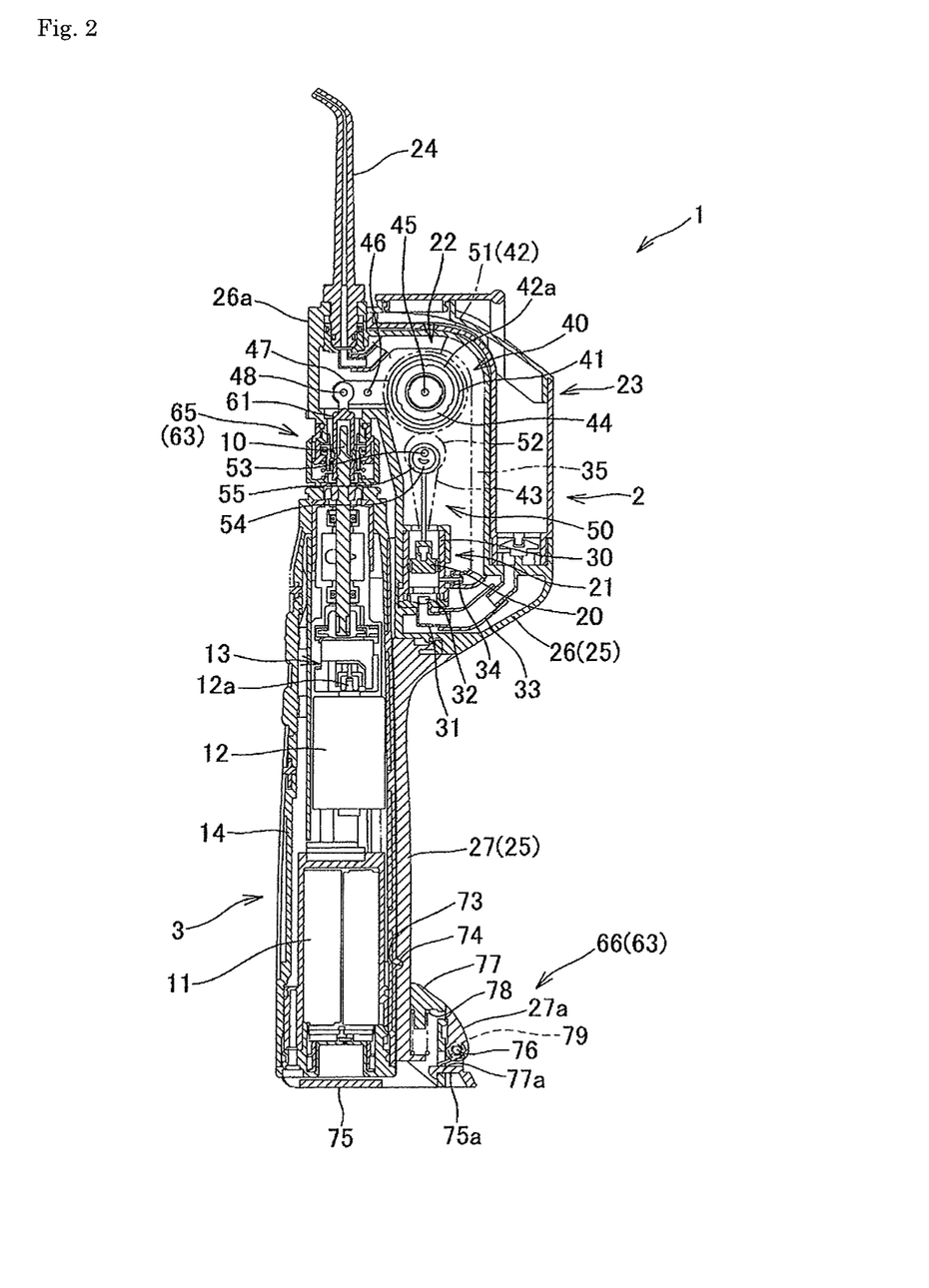
FIG. 2 is a cross section view of the water flow type oral cavity cleaning device at a placement position of a nozzle.
Figure 3:
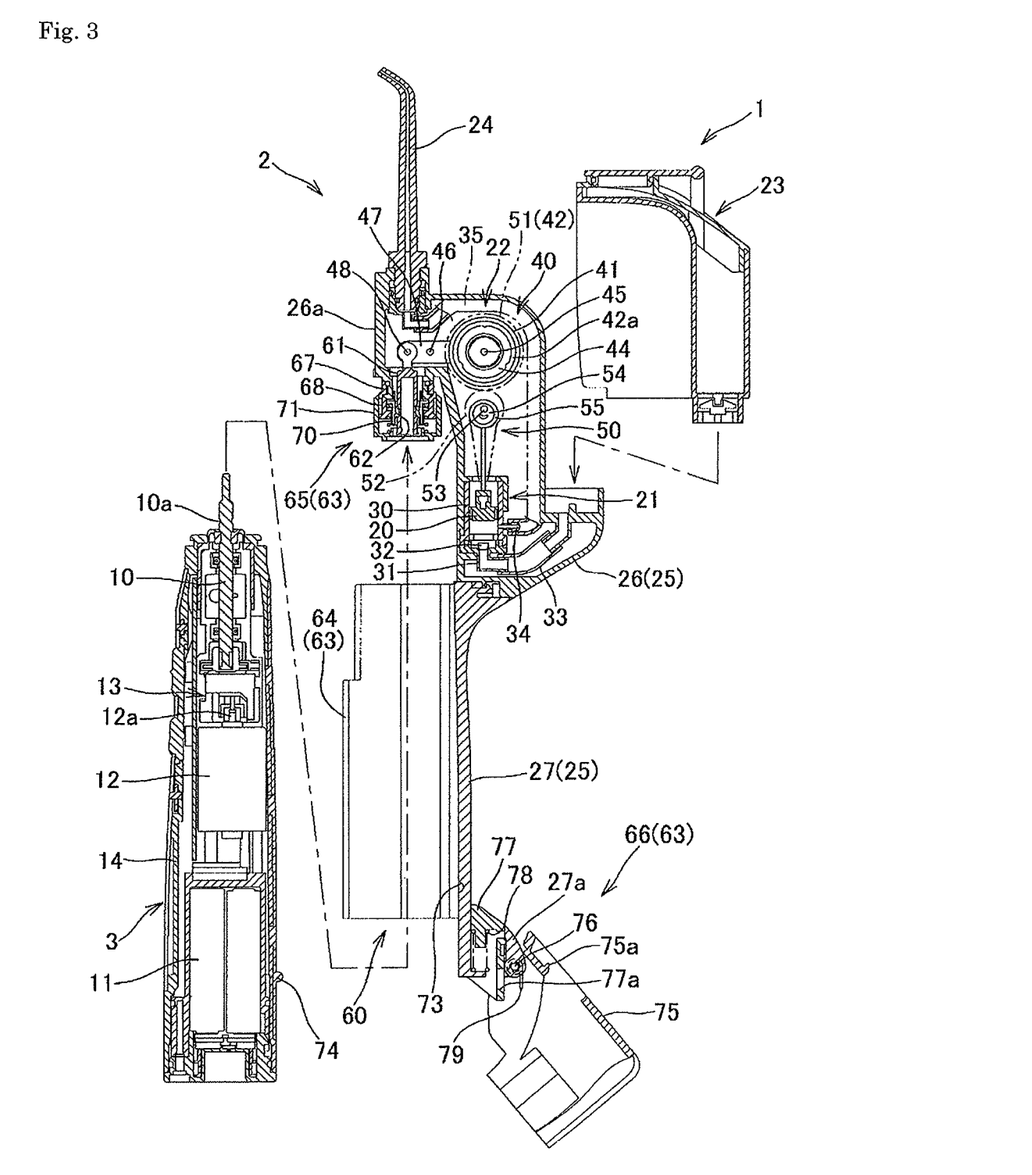
FIG. 3 is a diagram for describing an attachable/detachable part of the water flow type oral cavity cleaning device.
Figure 4:
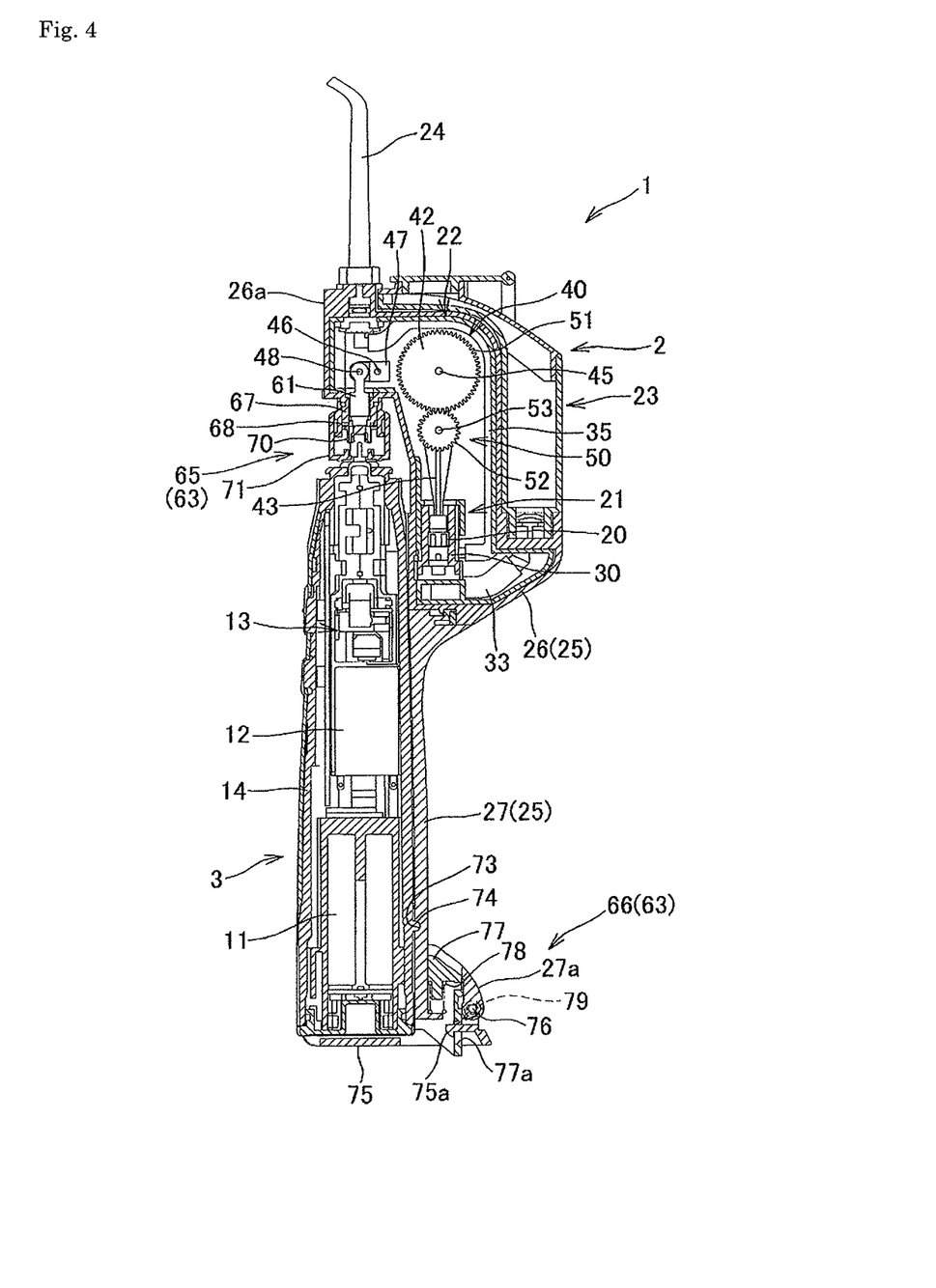
FIG. 4 is a cross section view of the water flow type oral cavity cleaning device at a placement position of a gear.

The positioning means 66 will be described below. As shown in FIGS. 1 to 4, a lock concave part 73 is formed in a front surface of a lower portion of the grip part 27, a projection 74 to be fitted to the lock concave part 73 is formed in a back surface of the casing 14 of the drive unit 3. When the projection 74 is fitted to the lock concave part 73, the drive unit 3 is placed at the cleaning device main body 2 in an appropriate position along an axial direction (height direction) of the drive shaft 10. A bracket part 27a is formed to project backward at a lower end portion of the grip part 27. A holder member 75 capable of holding the lower end portion of the drive unit 3 is supported at the bracket part 27a so as to rotatable about the pivotal support pin 76, ranging from a holding position shown in FIG. 2 to an opening position shown in FIG. 3. A twisted spring 79 is externally attached to the pivotal support pin 76 between the bracket part 27a and the holder member 75, and the holder member 75 is constantly biased toward the opening position via the twisted spring 79. A release button 77 is provided at the bracket part 27a so as to be movable in the up-down direction, and the release button 77 is constantly biased upward by a spring member 78. The holder member 75 has an engagement pawl 75a, and the release button 77 has a lock hole 77a in which the engagement pawl 75a can be locked. When the holder member 75 is operated so as to move from the opening position shown in FIG. 3 to the holding position, the engagement pawl 75a engages in the lock hole 77a, the holder member 75 is held at the holding position, and the lower end portion of the drive unit 3 is held so as not to move downward or forward with respect to the holder member 75, so that the projection 74 does not come off from the lock concave part 73, as shown in FIG. 2. Meanwhile, when the release button 77 is pressed, the engagement pawl 75a is disengaged from the lock hole 77a as shown in FIG. 4, and the holder member 75 rotates into the opening position by a biasing force of the twisted spring 79, as shown in FIG. 3, whereby the drive unit 3 can be attached to or detached from the cleaning device main body 2.

Figure 8:
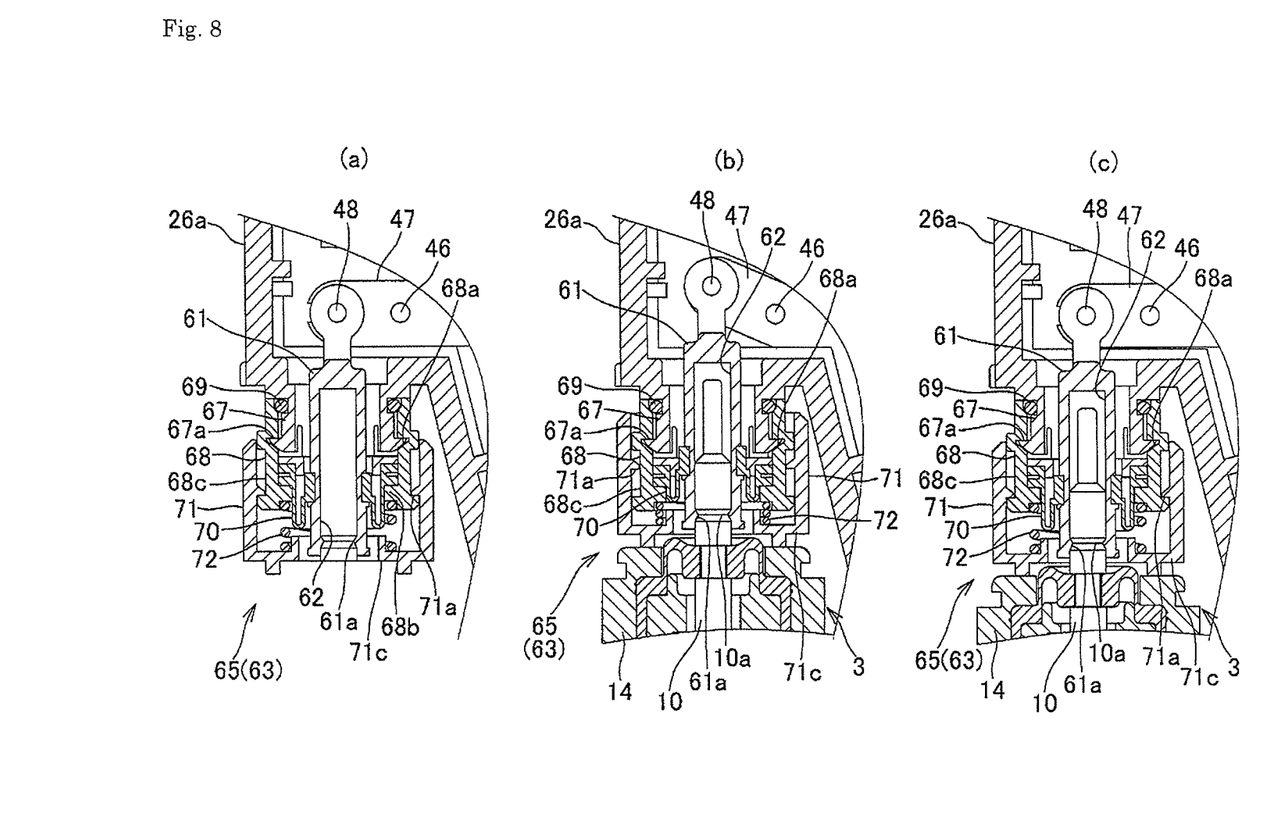
FIGS. 8(a) to 8(c) are diagrams for describing an operation of an attachment.
Figure 9:
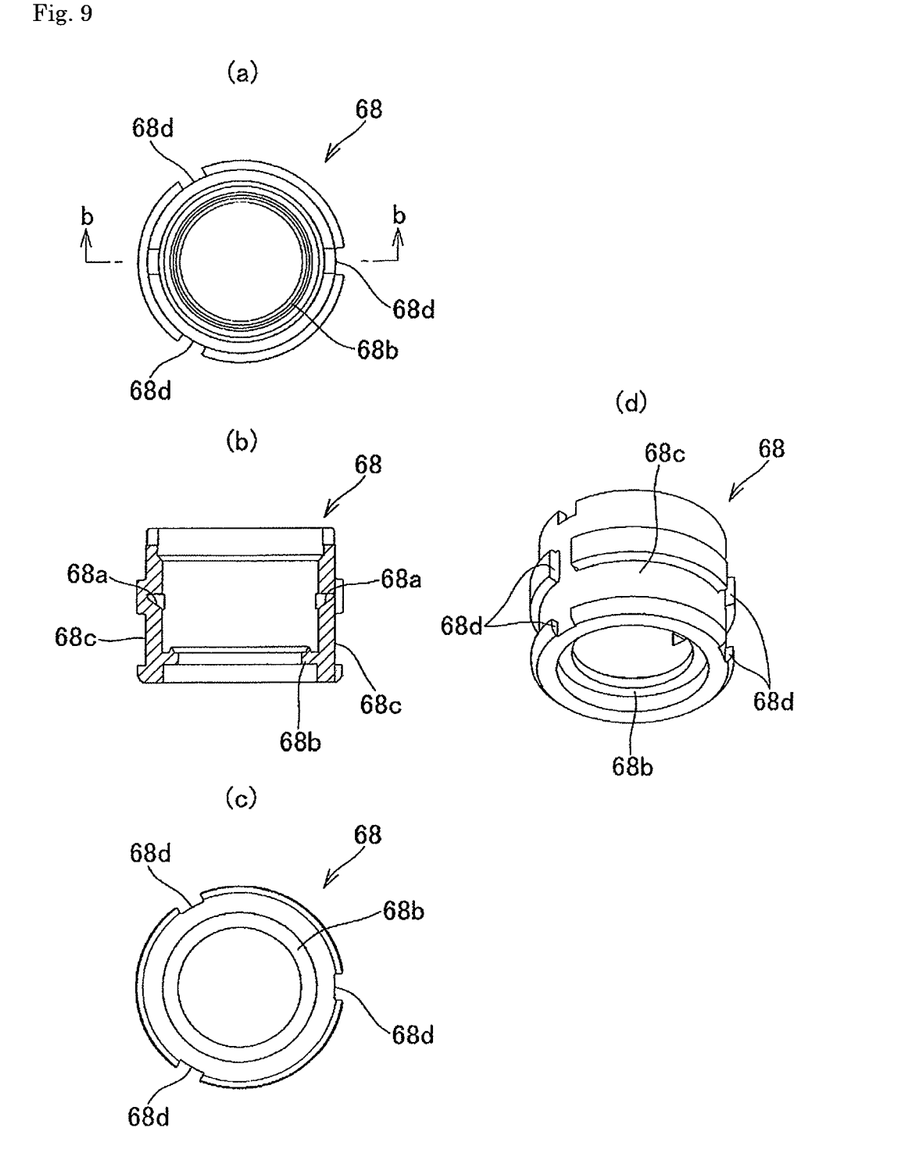
FIG. 9(a) is a plan view of a coupling tube.
FIG. 9(b) is a cross section view of the same taken along line b-b.
FIG. 9(c) is a bottom view of the same.
FIG. 9(d) is a perspective view of the same.
Figure 10:
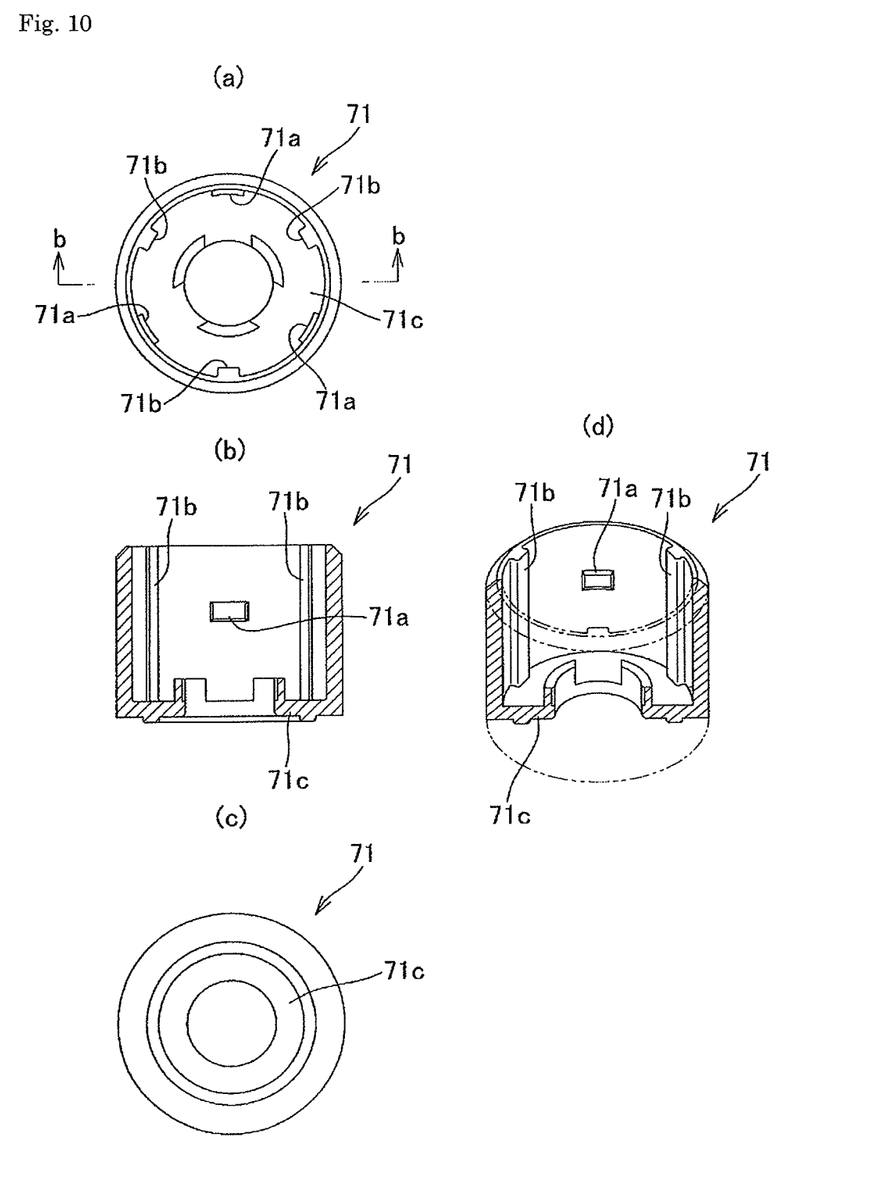
FIG. 10(a) is a plan view of a pressure tube.
FIG. 10(b) is a cross section view of the same taken along line b-b.
FIG. 10(c) is a bottom view of the same.
FIG. 10(d) is a perspective view of the same with a front half part cut out.

In the power transfer attachment 60, when the drive unit 3 is not assembled into the cleaning device main body 2, the pressure tube 71 is projected downward by the first bias means 65, and the power transfer member 61 is held by the second bias means 70 at a central position of a reciprocating linear motion in the up-down direction, as shown in FIG. 8 (a). In this state, the drive shaft 10 is inserted into the fitting part 62 until the annular groove 30a of the drive shaft 10 in the drive unit 3 of the electrical toothbrush is fitted to the annular projection 61a of the power transfer member 61 of the attachment 60, and the power transfer member 61 is pressed upward while the pressure tube 71 is pressed up by the casing 14 of the drive unit 3 to compress the first bias means 65, whereby the drive shaft 10 is fitted and fixed to the fitting part 62 of the power transfer member 61, as shown in FIG. 8 (b). At that time, the drive shaft 10 does not move relative to the drive unit 3, but the power transfer member 61 moves relative to the cleaning device main body 2 toward a top dead point. In addition, in this state, when the drive unit 3 is released, as shown in FIG. 8 (c), the drive unit 3 moves downward by a biasing force of the first bias means 65 until the projection 74 of the casing 14 of the drive unit 3 is locked at the lock concave part 73, and the power transfer member 61 moves downward together with the drive unit 3. While the casing 14 of the drive unit 3 is locked at the lock concave part 73, the current position of a reciprocating linear motion of the power transfer member 61 with respect to the cleaning device main body 2 is adjusted to a position adapted to the current position of a reciprocating linear motion of the drive shaft 10 with respect to the drive unit 3. Accordingly, synchronization is achieved between the reciprocating linear motion of the drive shaft 10 with respect to the drive unit 3 and the reciprocating linear motion of the power transfer member 61 with respect to the cleaning device main body 2.

As described above, in the power transfer attachment 60, the drive unit 3 of the electric toothbrush can be used also as a drive unit of the cleaning device main body 2, which makes it possible to use the electric toothbrush and the water flow type oral cavity cleaning device 1 while reducing an economic burden on a user. In addition, the position adjustment means 63 allows synchronization by a one-touch operation between the reciprocating linear motion of the drive shaft 10 with respect to the drive unit 3 and the reciprocating linear motion of the power transfer member 61 with respect to the cleaning device main body 2. Accordingly, it is possible to eliminate an adjustment task for synchronization and use the cleaning device main body 2 only by fitting the drive shaft 10 to the fitting part 62 of the power transfer member 61.

In the embodiment described above, the vibrational frequency adjustment device of the present invention is applied to the vibrational frequency adjustment means 22 of the water flow type oral cavity cleaning device 1. However, the vibrational frequency adjustment device can also be applied to various devices requiring modification of vibrational frequency or amplitude of a reciprocating linear motion.

REFERENCE SIGNS LIST

1 Water flow type oral cavity cleaning device
2 Cleaning device main body
3 Drive unit
10 Drive shaft
11 Battery
12 Motor
12a Rotation shaft
13 Scotch yoke mechanism
14 Casing
20 Piston
21 Pump
22 Vibrational frequency adjustment means
23 Cleaning liquid tank
24 Discharge nozzle
25 Frame
26 Base part
26a Front part
27 Grip part
27a Bracket part
30 Cylinder
30a Annular groove
31 Entrance part
32 Valve member
33 Supply tube
34 Exit part
35 Discharge tube
40 First conversion means
41 Input-side rotational member
41a Input-side sleeve
Output-side rotational member
42a Output-side sleeve
42b Projection
43 Second shaft member
44 One-way clutch
45 Support shaft
46 Pivotal support shaft
47 Lever member
47a Frame part
47b Long hole
48 Pin member
49 Operation pin
50 Second conversion means
51 First gear
52 Second gear
53 Pin member 54 Eccentric cam
55 Tubular part
60 Power transfer attachment
61 Power transfer member
61a Annular projection
62 Fitting part
63 Position adjustment means
64 Guide part
65 First bias means
66 Positioning means
67 Support tubular part
67a Hook part
68 Coupling tube
68a Fitting concave part
68b Holding part
68c Annular groove
68d Guide groove
69 Ring
70 Second bias means
71 Pressure tube
71a Engagement projection
71b Projecting rail
71c Reception part
72 Spring member
73 Lock concave part
74 Projection
75 Holder member
75a Engagement pawl
76 Pivotal support pin
77 Release button
77a Lock hole
78 Spring member
79 Twisted spring

The invention claimed is:

1. A vibrational frequency adjustment device, comprising:
a first conversion device that includes an input-side rotational member, an output-side rotational member, and a one-way clutch transferring only a rotational motion of the input-side rotational member in one direction to the output-side rotational member, the one-way clutch allows the input-side rotational member to make a reciprocating rotational motion by a set angle by a reciprocating linear motion of a first shaft member, thereby to transfer only a forward motion or a backward motion of the input-side rotational member to the output-side rotational member via the one-way clutch and rotate the output-side rotational member by each specific angle; and
a second conversion device that converts the rotational motion of the output-side rotational member into a reciprocating linear motion of a second shaft member, the second conversion device including a first gear formed at an outer peripheral part of the output-side rotational member, a second gear engaging with first gear, and an eccentric cam allowing the second shaft member to make the reciprocating linear motion is arranged at the second gear.

2. The vibrational frequency adjustment device according to claim 1, wherein the first conversion device is provided with a lever member that converts the reciprocating linear motion of the first shaft member into the reciprocating rotational motion of the input-side rotational member.

3. The vibrational frequency adjustment device according to claim 2, wherein the second conversion device is configured in such a manner that a first gear is formed at an outer peripheral part of the output-side rotational member, a second gear engaging with the first gear is provided, and an eccentric cam, allowing the second shaft member to make the reciprocating linear motion, is arranged at the second gear.

4. A water flow oral cavity cleaning device, comprising:
a pump capable of discharging a cleaning liquid by a reciprocating linear motion of a piston;
pump drive means driving the piston; and a discharge nozzle for the cleaning liquid, wherein
the pump drive means includes the vibrational frequency adjustment device according to claim 2 and a drive means main body having the first shaft member making the reciprocating linear motion,
the input-side rotational member is allowed to make the reciprocating rotational motion by the set angle by the reciprocating linear motion of the first shaft member, thereby to transfer only a forward motion or a backward motion of the input-side rotational member to the output-side rotational member via the one-way clutch and rotate the output-side rotational member by each specific angle, and the rotational motion of the output-side rotational member is converted into the reciprocating linear motion of the second shaft member, thereby to allow the piston to make the reciprocating linear motion at the second shaft member.

5. The water flow oral cavity cleaning device according to claim 4, wherein the drive means main body is used also as a drive unit of a sonic electric toothbrush.

6. The water flow oral cavity cleaning device according to 4, wherein the first shaft member and the nozzle are arranged in a coaxial line.

7. The water flow oral cavity cleaning device according to claim 4, wherein a pump and a cleaning liquid tank storing the cleaning liquid are provided above a handling grip part.

8. The water flow oral cavity cleaning device according to claim 4, wherein a drive unit of an electric toothbrush including a drive shaft as the first shaft member making the reciprocating linear motion, is detachably provided as the drive means main body to a cleaning device main body having the pump, the discharge nozzle, and the vibrational frequency adjustment device, and a power transfer attachment transferring power of the drive unit to the first conversion device, is provided, the power transfer attachment including:
a power transfer member that has a fitting part fitted and fixed detachably to the first shaft member of the drive unit and transfers power of the first shaft member to the first conversion device; and a position adjustment device that moves the drive unit and the cleaning device main body relatively in an axial direction of the first shaft member, thereby to adjust the current position of the reciprocating linear motion of the power transfer member moving together with the first shaft member of the drive unit with respect to the cleaning device main body to a position adapted to the current position of the reciprocating linear motion of the first shaft member with respect to the drive unit.

9. The water flow oral cavity cleaning device according to claim 4, wherein the first conversion device is provided with a lever member converting the reciprocating linear motion of the first shaft member into the reciprocating rotational motion of the input-side rotational member, and the power transfer member is coupled to an end part of the lever member.

10. The water flow oral cavity cleaning device according to claim 4, wherein the position adjustment device includes first bias means that is compressed by a fitting operation of the first shaft member into the fitting part to bias the drive unit in a direction of separation of the first shaft member; and a positioning device that locks movement of the drive unit by the first bias means in the direction of separation and places the drive unit in an appropriate position with respect to the cleaning device main body.

11. The water flow oral cavity cleaning device according to claim 4, wherein second bias means is provided to bias the power transfer member making the reciprocating linear motion together with the first shaft member to a central position of a reciprocating linear motion of the power transfer member.

12. The water flow oral cavity cleaning device according to claim 4, wherein a guide part guiding the drive unit movably only in a direction of fitting of the first shaft member to the fitting part, is provided.

13. A water flow oral cavity cleaning device, comprising:
a pump capable of discharging a cleaning liquid by a reciprocating linear motion of a piston;
pump drive means driving the piston; and a discharge nozzle for the cleaning liquid, wherein
the pump drive means includes the vibrational frequency adjustment device according to claim 1 and a drive means main body having the first shaft member making the reciprocating linear motion,
the input-side rotational member is allowed to make the reciprocating rotational motion by the set angle by the reciprocating linear motion of the first shaft member, thereby to transfer only a forward motion or a backward motion of the input-side rotational member to the output-side rotational member via the one-way clutch and rotate the output-side rotational member by each specific angle, and the rotational motion of the output-side rotational member is converted into the reciprocating linear motion of the second shaft member, thereby to allow the piston to make the reciprocating linear motion at the second shaft member.

14. The water flow oral cavity cleaning device according to claim 13, wherein the drive means main body is used also as a drive unit of a sonic electric toothbrush.

15. The water flow oral cavity cleaning device according to claim 13, wherein the first shaft member and the nozzle are arranged in a coaxial line.

16. The water flow oral cavity cleaning device according to claim 13, wherein a pump and a cleaning liquid tank storing the cleaning liquid are provided above a handling grip part.

17. The water flow oral cavity cleaning device according to claim 13, wherein a drive unit of an electric toothbrush including a drive shaft as the first shaft member making the reciprocating linear motion, is detachably provided as the drive means main body to a cleaning device main body having the pump, the discharge nozzle, and the vibrational frequency adjustment device, and a power transfer attachment transferring power of the drive unit to the first conversion device, is provided, the power transfer attachment including: a power transfer member that has a fitting part fitted and fixed detachably to the first shaft member of the drive unit and transfers power of the first shaft member to the first conversion device; and a position adjustment device that moves the drive unit and the cleaning device main body relatively in an axial direction of the first shaft member, thereby to adjust the current position of the reciprocating linear motion of the power transfer member moving together with the first shaft member of the drive unit with respect to the cleaning device main body to a position adapted to the current position of the reciprocating linear motion of the first shaft member with respect to the drive unit.

18. The water flow oral cavity cleaning device according to claim 17, wherein the first conversion device is provided with a lever member converting the reciprocating linear motion of the first shaft member into the reciprocating rotational motion of the input-side rotational member, and the power transfer member is coupled to an end part of the lever member.

19. The water flow oral cavity cleaning device according to claim 17, wherein the position adjustment device includes first bias means that is compressed by a fitting operation of the first shaft member into the fitting part to bias the drive unit in a direction of separation of the first shaft member; and a positioning device that locks movement of the drive unit by the first bias means in the direction of separation and places the drive unit in an appropriate position with respect to the cleaning device main body.

20. The water flow oral cavity cleaning device according to claim 17, wherein second bias means is provided to bias the power transfer member making the reciprocating linear motion together with the first shaft member to a central position of the reciprocating linear motion of the power transfer member.

21. The water flow oral cavity cleaning device according to claim 17, wherein a guide part guiding the drive unit movably only in a direction of fitting of the first shaft member to the fitting part, is provided.

* * * * *